US009510761B2

(12) United States Patent
Areny et al.

(10) Patent No.: US 9,510,761 B2
(45) Date of Patent: Dec. 6, 2016

(54) METHOD AND APPARATUS FOR OBTAINING CARDIOVASCULAR INFORMATION BY MEASURING BETWEEN TWO EXTREMITIES

(75) Inventors: Ramon Pallàs Areny, Barcelona (ES); Ramon Casanella Alonso, Barcelona (ES); Joan Gómez Clapers, Barcelona (ES)

(73) Assignee: UNIVERSITAT POLITÈCNICA DE CATALUNYA, Barcelona (ES)

( * ) Notice: Subject to any disclaimer, the term of this patent is extended or adjusted under 35 U.S.C. 154(b) by 0 days.

(21) Appl. No.: 14/235,588

(22) PCT Filed: Jul. 26, 2012

(86) PCT No.: PCT/ES2012/070574
§ 371 (c)(1),
(2), (4) Date: Jan. 28, 2014

(87) PCT Pub. No.: WO2013/017718
PCT Pub. Date: Feb. 7, 2013

(65) Prior Publication Data
US 2014/0194721 A1    Jul. 10, 2014

(30) Foreign Application Priority Data
Jul. 29, 2011 (ES) .................................. 201131331

(51) Int. Cl.
*A61B 5/04* (2006.01)
*A61B 5/0295* (2006.01)
(Continued)

(52) U.S. Cl.
CPC ......... *A61B 5/0295* (2013.01); *A61B 5/02125* (2013.01); *A61B 5/0404* (2013.01);
(Continued)

(58) Field of Classification Search
USPC ........................................................ 600/483
See application file for complete search history.

(56) References Cited

U.S. PATENT DOCUMENTS 6,228,033 B1 * 5/2001 Koobi ............... A61B 5/02007
600/483

FOREIGN PATENT DOCUMENTS

| EP | 2 305 111 | 4/2011 |
|---|---|---|
| EP | 2 308 372 | 4/2011 |
| WO | WO 2005/ 010640 | 2/2005 |
| WO | WO 2011/ 075767 | 6/2011 |

OTHER PUBLICATIONS

M.L. Simoons, M.D., et al., "Gradual Changes of ECG Waveform During and After Exercise in Normal Subjects," American Heart Association, *Circulation: Journal of the American Heart Association*, vol. 52, Oct. 1975, pp. 570-577 and title page.
(Continued)

*Primary Examiner* — Nicole F Johnson
(74) *Attorney, Agent, or Firm* — Staas & Halsey LLP

(57) ABSTRACT

A method and an apparatus for obtaining information on a cardiovascular system beat by beat and continuously which are based exclusively on measurements between two limbs and effected with a pair of distal electrodes on each limb. The measurement is made by causing an alternating current to flow between one electrode of each limb and measuring the potential difference between the other two electrodes, one also on each limb. This potential difference has a low frequency component which is an electrocardiogram (ECG) and another component having a frequency of the injected alternating current and from which an impedance plethysmogram (IPG) is extracted. The cardiovascular information is determined by measuring the time interval between any predefined characteristic element of the ECG and one of the IPG.

16 Claims, 3 Drawing Sheets

(51) Int. Cl.
   *A61B 5/00*     (2006.01)
   *A61B 5/0404*   (2006.01)
   *A61B 5/053*    (2006.01)
   *A61B 5/0408*   (2006.01)
   *A61B 5/021*    (2006.01)

(52) U.S. Cl.
   CPC ......... *A61B5/0408* (2013.01); *A61B 5/04012* (2013.01); *A61B 5/0535* (2013.01); *A61B 5/6824* (2013.01); *A61B 5/6825* (2013.01); *A61B 5/6828* (2013.01); *A61B 5/6829* (2013.01)

(56) References Cited

OTHER PUBLICATIONS

Gary G. Berntson, et al., "Where to Q in PEP," Society for Psychophysiological Research, *Psychophysiology*, vol. 41, 2004, pp. 333-337.

Delphion English Abstract of European Application No. EP 2 308 372, Published Apr. 13, 2011.

Delphion English Abstract of European Application No. EP 2 305 111, Published Apr. 6, 2011.

Patent Abstracts of Japan, Publication No. 2009050508, Published Mar. 12, 2009.

Gómez-Clapers J et al., "*Pulse Arrival Time Estimation from the Impedance Plethysmogram Obtained with a Handheld Device*", 33rd Annual International Conference of the IEEE EMBS, Boston, MA, USA, Aug. 30-Sep. 3, 2011, pp. 516-519.

Eliakim, Marcel, M.D., F.A.C.C. et al., "*Pulse Wave Velocity in Healthy Subjects and in Patients with Various Disease States*", American Heart Journal, Oct. 1971, vol. 82, No. 4, pp. 448-457.

Chen, W et al., "*Continuous Estimation of Systolic Blood Pressure Using the Pulse Arrival Time and Intermittent Calibration*", Medical & Biological Engineering & Computing 2000, vol. 38, pp. 569-574.

Bang, Suyoung et al., "*A Pulse Transit Time Measurement Method Based on Electrocardiography and Bioimpedance*", Jul. 2009, IEEE, pp. 153-156.

International Search Report dated Jan. 18, 2013 in corresponding PCT/ES2012/070574.

* cited by examiner

METHOD AND APPARATUS FOR OBTAINING CARDIOVASCULAR INFORMATION BY MEASURING BETWEEN TWO EXTREMITIES

CROSS REFERENCE TO RELATED APPLICATIONS

This application claims the benefit under 35 U.S.C. Section 371, of PCT International Application No. PCT/ES2012/070574, filed Jul. 26, 2012, and under 35 U.S.C. §119 of Spanish Application No. P201131331 filed Jul. 29, 2011, the contents of which are incorporated herein by reference.

FIELD OF THE INVENTION

Measuring and control instrumentation. The present invention relates in general to noninvasive physiological parameter measuring and monitoring systems.

BACKGROUND ART

Obtaining information on cardiovascular parameters is of great importance for ascertaining people's state of health. The availability of an apparatus which can obtain said information beat by beat continuously, simply and comfortably, without requiring the user themselves or an assistant to have any specific abilities or training, is of great interest. Particularly, when the measurements are not taken in clinical or health care environments it is very desirable for the subject not to need any aid to be able to take the measurement.

Among the noninvasive measures providing information on the cardiovascular system, the bioelectric signal measurements are some of the easiest to obtain, above all if taken with dry electrodes (without conducting gel). This practice limits the measuring areas to the limbs (arms and legs) because the mechanical contact with the electrodes may be made by fixing them or holding them in the hand or resting the hands or feet on them. The application of electrodes to other parts of the body, the thorax for example, requires them to be held with means achieving a sufficient pressure to guarantee a good contact, which involves an obvious inconvenience and requires time for placing them.

Two bioelectric signals that provide information on the cardiovascular system are the electrocardiogram (or ECG) and the electrical impedance signals measured in volumes of the body where there is a variation attributable to the blood flow. The measurement of volume changes (plethysmography) based on measuring the electrical impedance is called impedance plethysmography (IPG). Plethysmography based on measuring the light absorbency is called photoplethysmography (PPG)

The ECG and IPG provide information on the cardiovascular system not only separately but also jointly. To be precise, the time taken by the arterial pulse wave (involving a simultaneous change of volume) to reach a part of the body depends not only on the distance between said part and the heart, but it also depends on the diameter, thickness and stiffness of the arteries, and on the rheological properties of the blood. A time including said information is the one known as PAT (pulse arrival time), which is of great diagnostic interest. See, for example, Eliakim et al, *Pulse wave velocity in healthy subjects and in patients with various disease states*, American Heart Journal, vol. 82, no 4, pp 448-457, October 1971. Particularly, the PAT measured between the R wave of the ECG and the foot (starting point of the rapid rise associated with the ventricular systole) of the photoplethysmography (PPG) in a finger of one hand is frequently used to estimate the systolic pressure, for example, as described by Chen et al., in *"Continuous estimation of systolic blood pressure using the pulse arrival time and intermittent calibration"; Medical and Biological Engineering and Computing*, vol. 38, pp. 569-574, 2000. Since both the PPG and the IPG measure changes of volume, the wave forms of both signals are analogous, and therefore the IPG has been used as an alternative signal to the PPG to measure time intervals related with the propagation of the pulse wave in the arteries In the document by Bang et al. *"A pulse transit time measurement method based on electrocardiography and bioimpedance" Biomedical Circuits and Systems Conference* (BioCAS) 2009, pp. 153-156 the time elapsed between the ECG R wave, obtained with an electrode on each arm, and the IPG peak, obtained with four electrodes on the forearm, was measured and this time was compared with the time elapsed between the ECG R wave and the PPG peak. The correlation between both times was excellent. Although this method proposed by Bang et al. has the advantage of not requiring electrodes on the thorax, the use of conventional electrodes (with conducting gel) adhered to the arm to obtain the ECG and IPG makes the process slow and uncomfortable.

Another document where the measuring of physiological parameters by the ECG and IPG without the necessity of locating electrodes on the thorax is described in U.S. Pat. No. 6,228,033 for Apparatus and methods for a noninvasive measurement of physiological parameters, to Kööbi et al., 2001. In this patent the IPG is preferably obtained by injecting a current between both arms and both legs at the same time, and detecting also at the same time between both arms and both legs. In this regard, see FIG. 1 herein, where the injection electrodes are the pair 31 and the pair 32, and the detection electrodes are the pair 11 and the pair 12. In a preferred embodiment a detection electrode 11 is about 5 cm from an adjacent injection electrode 31. With these electrode connections, it is stated in said patent that the IPG obtained reflects above all the overall impedance changes between arms and legs, which will be proportional to the pumping out of blood from the left ventricle. To obtain a distal pulse wave, Kööbi et al. obtain the IPG in a segment of one limb, by using a further two electrodes (21 and 22). They obtain the ECG with the same electrodes (pair 11 and pair 12) with which there is detected the potential difference created by the injected current to measure the impedance without needing thoracic electrodes. The same document describes that the injection of current to obtain the overall IPG is always at least between one arm and one leg; a possible arrangement of the electrodes according to this embodiment is shown in FIG. 2 herein where the injection is through the electrode 31 and electrode 32 and the detection is through the electrode 11 and the electrode 12. However, according to Kööbi et al, even in this embodiment wherein injection occurs only through one arm and one foot, to obtain the distal pulse wave by the IPG in a segment of one limb a further two detection electrodes (21 and 22) disposed along said segment are still necessary. It is concluded, therefore, that according to the method described in U.S. Pat. No. 6,228,033 simultaneously to obtain a distal pulse wave and the ECG, at least six electrodes are required, although there is obtained also another IPG basically reflecting the impedance changes in the thorax. To obtain the transit time of the pulse wave to a distal segment, they calculate the distance between the peaks of both impedance signals obtained, one from the voltage detected between the electrode 11 and the electrode 12 (FIG. 2) or between the pair of electrodes 11 and the pair of electrodes 12 (FIG. 1) and the other from the voltage detected between the electrodes 21 and 22.

On the other hand, this Kööbi et al. patent is contemplated for clinical environments and perhaps for this reason they consider the possibility of using electrodes with gel as an advantage, since they are common in electrocardiography. In fact, the four electrodes at least necessary for the limbs (11, 12, 31 and 32 in FIG. 2) could be replaced by dry electrodes. On the other hand, if the two electrodes (21 and 22 in FIG. 2) required for obtaining a local pulse wave by the IPG in a segment of a limb were dry, they would have to be held in place by a strap or other similar means. Furthermore the need always to have a connection with at least one arm and one leg does not favor the design of a system so compact as may be needing only both hands or both feet.

The use of electrodes on the limbs and on different parts of the thorax to measure therebetween the overall electrical impedance and the electrical impedance at different sections of the body, and the changes thereof over time is also described in the document WO 2005/010640 "Non-invasive multi-channel monitoring of hemodynamic parameters" to Tsoglin and Margolin, 2005. But, to measure the peripheral blood flow they use, for example, additional electrodes on one finger (page. 13 and FIGS. 1, 2I, 3A, 3B, 3C, 4C and 5). Furthermore, although some of the electrodes used for measuring the bioimpedance are also used to obtain the ECG, they do not do so simultaneously, but the apparatus includes a switching circuit (member 29 in FIG. 6 of the document) connecting the electrodes for carrying out one function or the other, but never both together, whereby it is not possible to obtain cardiovascular information from the combination of the simultaneous measurements of both.

SUMMARY OF THE INVENTION

The method and apparatus proposed in the invention described hereinafter allow the ECG and a distal pulse wave to be obtained using only two pairs of electrodes, dry or otherwise, it being sufficient for one pair to be in contact with each of the two upper limbs or with each of the two lower limbs, although also one pair may be disposed on one arm and the other pair on one leg, either on the same side or on opposite sides of the body.

The present invention allows information on the cardiovascular system to be obtained beat by beat and continuously, by measuring only between two limbs with one pair of distal electrodes on each of them. To this end, an alternating current is injected between both limbs and the potential difference is measured between two electrodes, each being adjacent one of the two injection electrodes.

Referring to FIG. 3, the excitation signal 300 is an alternating current which is caused to flow between an electrode A which is on a distal segment of one limb and an electrode B which is on a distal segment of another limb. A further two electrodes C and D detect the potential in areas respectively close to each of the injection electrodes, and the potential difference between them is detected by the detection circuit 310. The first pair of electrodes 301 is on one limb and the second pair 302 is on another limb.

The voltage at the detector circuit 310 inlet has two components: one low frequency component (less than 40 Hz) which is the electrocardiogram (or ECG), generated by the body itself owing to the electrical activity of the heart, and a component having the frequency of the injected alternating current and the amplitude of which depends on the electrical impedance in the conducting volume through which said current flows. Said impedance has a continuous component of great relative amplitude, due to the basal electrical impedance between the limbs being measured, which will remain constant, and a much smaller variable component, due to the cardiovascular activity. The registration of this variable component of the electrical bioimpedance is the so-called impedance plethysmogram (IPG). Therefore, the IPG and the ECG may be separated at the detector circuit 310 outlet and each of these signals can be amplified by means of respective conventional amplifier circuits 320 and 330.

In their article "*Sources of error in tetrapolar impedance measurements on biomaterials and other ionic conductors*" published in the Journal of Physics D: Applied Physics, vol. 40, pp. 9-14, 2007, Grimnes and Martinsen warn that it would be erroneous to assume that when measuring with four electrodes the impedance is determined only by the volume between the detection electrodes and show that the volume between the injection electrodes and the detection electrodes also contributes to the impedance. Thus, the measured impedance will be the sum of the impedance of all the segments between the electrodes, each one weighted depending on the intrinsic electrical properties of each segment and its section, those of smaller section being the ones that will have a greater contribution to the total impedance measured.

When measuring between the distal segments of two limbs, the conducting volume between the injection electrodes is constituted by each limb and the thorax. Owing to its relative transversal dimensions, it is to be expected that the thoracic impedance is much smaller than that of the limbs. Effectively, S. Grimnes, in Table 3 of his article "*Impedance measurement of individual skin surface electrodes*" in Medical and Biological Engineering and Computing, vol. 21, pp. 750-755, 1983, shows that the impedance between the breastbone and the middle of the thigh is one third of the impedance between the breastbone and the center of the upper arm, one seventh of the impedance of one arm and one tenth of the impedance of a finger. With this data, since in this invention each electrode pair is disposed on the distal segments of a limb, it is to be expected that a major portion of the impedance obtained is due to the limb tissues, the section of which is much smaller than that of the thorax. Bearing in mind the abundant presence of arteries in the hands and in the feet, said local impedances will change with each beat due to the arrival of the arterial pressure pulse and the consequent volume change. Owing to the breathing and to the ejection of blood from the heart on each beat the thoracic impedance will also change, but since its section is much larger, the sensitivity of the electrodes to these changes at the thorax will be much lower than the sensitivity to the changes at the limbs themselves due to the arterial pressure wave.

Once the ECG and the IPG have been digitized, the propagation time of the pulse wave may be calculated by measuring the interval between the R wave of the ECG, for example, and a predefined element of the pulsing component of the impedance, such as the onset of its rapid variation, the point of maximum amplitude (peak), an intermediate point between both (for example, the one corresponding to 10% or 50% of the pulse amplitude), the maximum gradient point, or any other convenient element. These times are related to the elasticity of the arteries and the arterial pressure.

The identification and combination of the predefined elements in the ECG and the IPG may be effected by a processor 340 or an expert using cursors on the display monitor 350 and may be exported from the processor 340 as a reporting function 360. The processor may also calculate the amplitude of certain predefined points of the IPG, and with these amplitudes indices and parameters analogous to those defined in the literature for the equivalent points in the arterial pressure wave, and additional parameters which aid better to characterize the pulse wave form may be defined. The diagnostic value of the indices and parameters traditionally defined for the pressure wave in the cardiovascular system is well documented, for example in the book "*McDonald's blood flow in arteries*" edited by W. W. Nichols and M. F. O'Rourke and published by Hodder Arnold (London), 2005. Particularly, said indices are used to noninvasively assess the stiffness of the arteries. (See for example the publications "*Noninvasive assessment of arterial stiffness and risk of atherosclerotic events*" by Oliver and Webb in Arteriosclerosis, Thrombosis, and Vascular Biology, vol. 23, pp. 554-566, 2003, and "*Arterial stiffness and cardiovascular events: the Framingham heart study*" by Mitchell et al., in Circulation, vol. 121, pp. 505-511, 2010). With the present invention, it is possible to calculate said indices and parameters in signals obtained by measuring with only four electrodes between both hands, between both feet, or between one hand and one foot, either on the same side of the body or on opposite sides.

Since in this method there is no need to apply electrodes on the body trunk or necessarily on segments of the limbs, but the contact with the electrodes may be made with the hands or feet, there is obtained the advantage of being able to use dry electrodes. Thus, the contact with them may be made, for example, with the fingers of the hands or with the soles of the feet, to mention two cases particularly comfortable for the user. But the proposed method does not of itself demand that the electrodes should be dry, but that they may use a conducting gel, for example on persons where, because some member has been amputated, the most distal end of a limb is a stump. However, if the electrodes are located on the body, the variability of their position is much wider than when the electrodes are on a surface with which a limb has to make contact, particularly if the contact is made with the fingers. Since the position of the electrodes affects the IPG wave form, guaranteeing that the position of the contacts is always the same is an important advantage.

DESCRIPTION OF EMBODIMENTS

Figure 1:
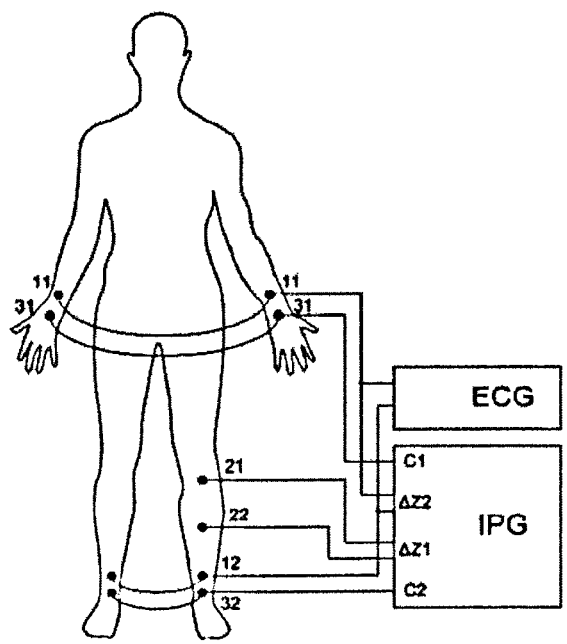
FIG. 1 shows the arrangement of the electrodes described in a preferred embodiment of U.S. Pat. No. 6,228,033, the designation of the electrodes being the same as in the original document.
Figure 2:
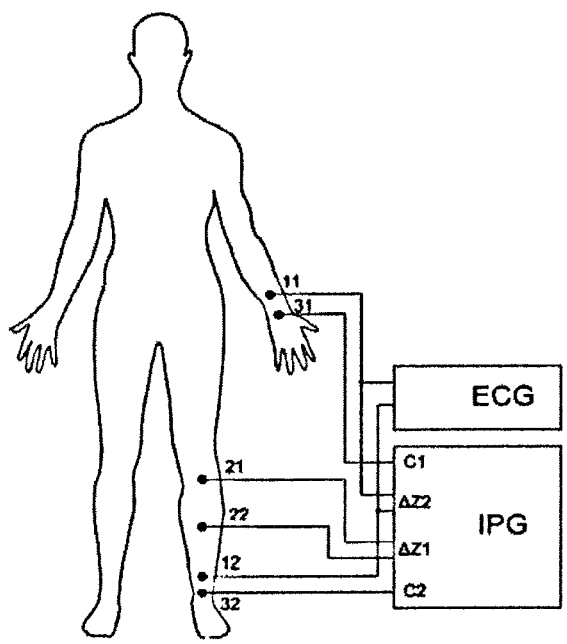
FIG. 2 shows the arrangement of the electrodes in a derivative embodiment of the preferred embodiment described in U.S. Pat. No. 6,228,033, the designation of the electrodes being the same as in the original document.
Figure 3:
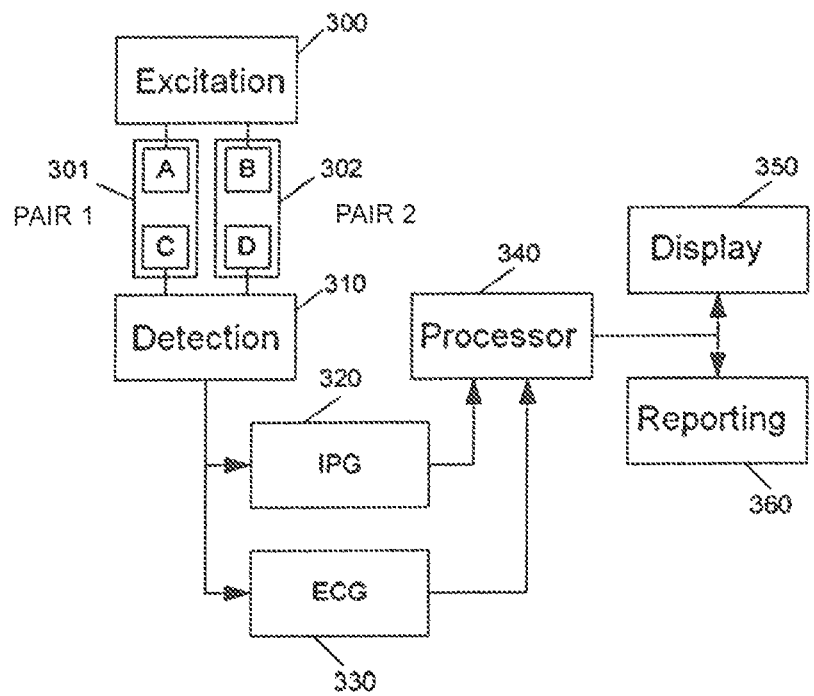
FIG. 3 is a block diagram of the proposed measuring method.
Figure 4:
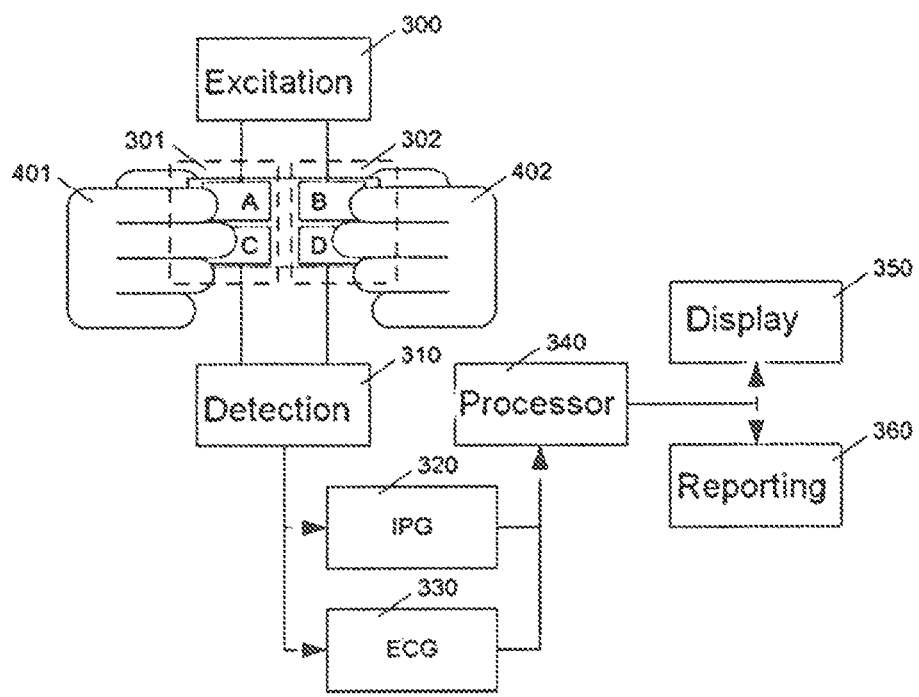
FIG. 4 shows a preferred embodiment of the method described in this invention.

FIG. 4 shows a preferred embodiment of the measuring method described and shown with the diagram of FIG. 3. In this preferred embodiment, both the electrode pair 301 and the electrode pair 302 are two copper sheets and both pairs are disposed on a common surface which the user holds with his/her hands, in such a way that the index finger of the right hand 401 is in contact with the electrode A of the pair 301 and the middle finger of the same hand is in contact with the electrode C of the same pair 301. At the same time, the index finger of the left hand 402 is in contact with the electrode B of the pair 302 and the middle finger of the same hand is in contact with the electrode D of the same pair 302.

An alternating current source generates the excitation signal 300 which is a sinusoidal current of 10 kHz and 0.5 mA peak, injected between the electrodes A and B; this second electrode B is connected to the signal earth of the electronic input circuits of the apparatus. The electrode C and electrode D are each connected to a unit gain amplifier, the ensemble of which constitutes the detector 310. The potential difference between the outlets of these two amplifiers is measured with two circuits with a differential input which are connected in parallel, one to obtain the IPG and the other to obtain the ECG. In this preferred embodiment, the circuit 320 for obtaining the IPG consists of a high pass filter with differential input and output, with cut-off frequencies of 1 kHz, followed by a six gain instrumentation amplifier, an amplitude demodulator based on a coherent detector formed by an amplifier, the gain of which is periodically switched between +1 and −1 synchronously with the carrier signal, a filter allowing the frequency band of 0.05 Hz to 30 Hz to pass, and a 14,000 gain output amplifier. The circuit 330 for obtaining the ECG consists of a filter having differential inlet and outlet allowing the frequency band of 0.05 Hz to 100 Hz to pass, followed by an instrumentation amplifier of 1000 gain and a low pass filter with a cut-off frequency of 100 Hz. Both the IPG and the ECG are digitized with a resolution of 16 bits and a sampling frequency of 10 kHz.

The specific elements defined for the ECG and the IPG in this preferred embodiment are the R wave of the ECG and the point on the rising flank of the IPG, the amplitude of which is equidistant from the foot and the peak of the impedance pulse.

Results

Figure 5:
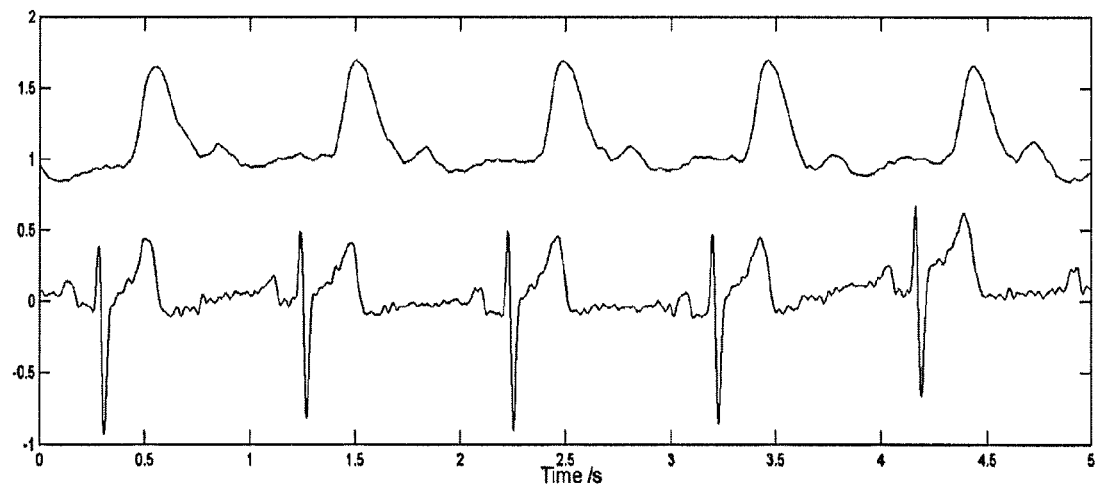
FIG. 5 shows the ECG and IPG obtained with the preferred embodiment of FIG. 4.

FIG. 5 shows the IPG and the ECG obtained with the described preferred embodiment. It may be seen that the peaks of the upper curve (the IPG) appear always with a considerable delay relative to the peaks of the lower curve, which are the R wave of the ECG. If the detected impedance changes were those produced on the thorax, the IPG peaks would appear shortly after the R wave, since this coincides with the ventricular systole and the consequent expulsion of blood from the heart. The long delay between the IPG peak and the ECG R wave confirms the advantage of the electrode arrangement proposed in this invention, where the injection electrodes are at a distal end of each of two limbs and the detection electrodes are close to the injection electrodes.

Figure 6:
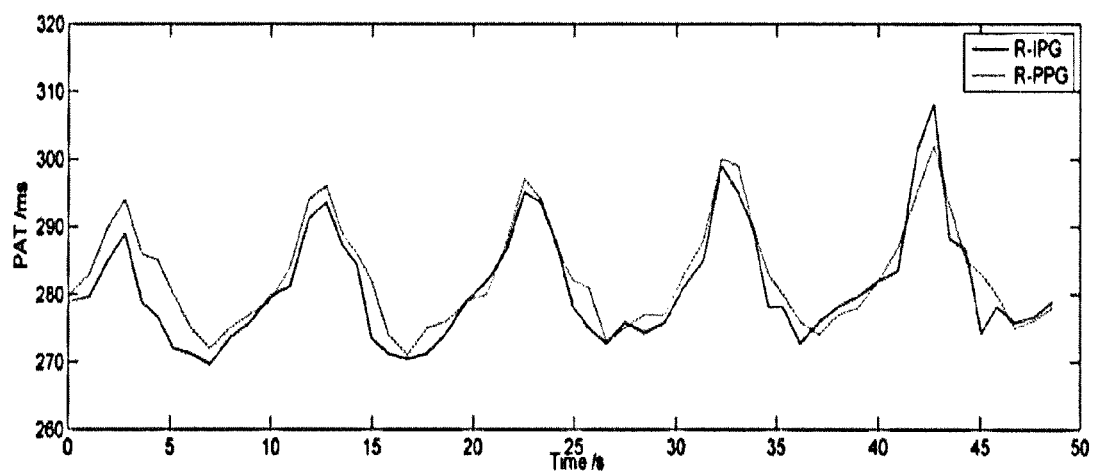
FIG. 6 shoes the evolution of the PAT measured with the proposed method (solid line) and the PAT measured with the conventional method (from the R wave of the ECG to a point of the PPG (photoplethysmogram)) along a periodic respiration at a rate of six respirations per minute.

To verify that the PAT interval measured between the two predefined points of the ECG and IPG signals, and identified in the preferred embodiment of this invention, are related to the changes in the propagation in the pulse wave, there has been carried out an experiment consisting of breathing with an approximately periodic frequency and comparing the PAT between the ECG and the IPG obtained with the method described in this invention with the PAT between the same ECG and IPG obtained with a commercial photoplethysmograph disposed on the ring finger of one hand; to be precise, the PAT was measured between the R wave and the point on the rising flank of the PPG, the amplitude of which is that of the foot of the PPG plus 10% of the difference between the peak and the foot of the PPG. It is well known that both the propagation velocity of the pulse wave and the arterial pressure depend on the breathing, since this causes variation in the intrathoracic pressure. FIG. 6 shows that, on breathing at about 0.1 Hz (approximately 6 inhalations per minute) the fluctuations in the PAT measured between the ECG and the IPG coincide closely approximately with the fluctuations of the PAT measured between the ECG and the PPG. The correlation coefficient between both signals displayed is 0.93.

Having sufficiently described the invention, as well as a preferred embodiment, it should only be added that it is possible to make modifications in its constitution, materials used and in the form and dimensions of the electrodes, without deviating from the scope of the invention defined in the following claims.

The invention claimed is:

1. A method for obtaining information on the cardiovascular system, comprising:
   a) injecting a current and measuring potential differences between two limbs, using a total of only four electrodes which are, for each of the two limbs, a pair of electrodes including one injector electrode and one measuring electrode close to each other and located on a distal segment thereof;
   b) obtaining an electrocardiogram from the measuring;
   c) obtaining an impedance plethysmogram from the measuring;
   d) identifying specific predefined elements in the electrocardiogram and the impedance plethysmogram;
   e) measuring time intervals between the specific predefined elements; and
   f) estimating a pulse arrival time from said time intervals.

2. The method of claim 1, wherein the electrodes of one pair make contact with two points of one hand and the electrodes of the other pair make contact with two points of the other hand.

3. The method of claim 1, wherein the electrodes of one pair make contact with two points of one foot and the electrodes of the other pair make contact with two points of the other foot.

4. The method of claim 1, wherein the electrodes of one pair make contact with two points of one hand and the electrodes of the other pair make contact with two points of one foot.

5. The method of claim 1, wherein the specific predefined elements are selected from a first predefined element in the electrocardiogram and a first predefined element in the impedance plethysmogram, and
   wherein the time intervals measured are between these first predefined elements.

6. The method of claim 1, wherein the specific predefined elements are selected from an onset of rapid variation, a point of maximum amplitude, an intermediate point, or a maximum gradient point.

7. The method of claim 6, wherein the intermediate point corresponds to 10% or 50% of a pulse amplitude.

8. The method of claim 1, wherein the specific predefined elements are selected to include an R wave.

9. A method for obtaining information on the cardiovascular system, consisting of:
   a) injecting a current and measuring potential differences between two limbs, using a total of only four electrodes which are, for each of the two limbs, a pair of electrodes including one injector electrode and one measuring electrode close to each other and located on a distal segment thereof;
   b) obtaining an electrocardiogram from the measuring;
   c) obtaining an impedance plethysmogram from the measuring;
   d) identifying specific predefined elements in the electrocardiogram and the impedance plethysmogram;
   e) measuring time intervals between the specific predefined elements; and
   f) estimating a pulse arrival time from said time intervals.

10. The method of claim 9, wherein the electrodes of one pair make contact with two points of one hand and the electrodes of the other pair make contact with two points of the other hand.

11. The method of claim 9, wherein the electrodes of one pair make contact with two points of one foot and the electrodes of the other pair make contact with two points of the other foot.

12. The method of claim 9, wherein the electrodes of one pair make contact with two points of one hand and the electrodes of the other pair make contact with two points of one foot.

13. The method of claim 9, wherein the specific predefined elements are selected from a first predefined element in the electrocardiogram and a first predefined element in the impedance plethysmogram, and
   wherein the time intervals measured are between these first predefined elements.

14. The method of claim 9, wherein the specific predefined elements are selected from an onset of rapid variation, a point of maximum amplitude, an intermediate point, or a maximum gradient point.

15. The method of claim 14, wherein the intermediate point corresponds to 10% or 50% of a pulse amplitude.

16. The method of claim 9, wherein the specific predefined elements are selected to include an R wave.

* * * * *